United States Patent [19]

Tenmyo et al.

[11] Patent Number: 5,266,600
[45] Date of Patent: Nov. 30, 1993

[54] BU-4641V, AN ANTIBACTERIAL, ANTIVIRAL AND ANTITUMOR ANTIBIOTIC

[75] Inventors: Osamu Tenmyo, Yokohama; Yosuke Sawada, Tokyo; Toshikazu Oki, Yokohama; Masahisa Oka, both of Yokohama; Masaru Sugawara, Tokyo; Noriyuki Ohkusa, Kawasaki, all of Japan; Pin-Fang Lin, Branford; Stephen W. Mamber, Wethersfield, both of Conn.

[73] Assignee: Bristol-Myers Squibb Company, New York, N.Y.

[21] Appl. No.: 969,606

[22] Filed: Oct. 30, 1992

Related U.S. Application Data

[63] Continuation-in-part of Ser. No. 843,659, Feb. 28, 1992, abandoned.

[51] Int. Cl.$^5$ ............... C07C 49/537; C07C 49/553; A61K 31/12; A01N 35/00
[52] U.S. Cl. .................................... 514/691; 568/374
[58] Field of Search .................... 568/374; 514/691

[56] References Cited

U.S. PATENT DOCUMENTS 3,816,534  6/1974  Lemberg et al. ............... 568/374
4,617,146  10/1986  Helmlinger et al. ............ 568/374
5,077,275  12/1991  Boden et al. .................. 568/374

FOREIGN PATENT DOCUMENTS 306282   3/1989  European Pat. Off.
2630428  1/1978  Fed. Rep. of Germany.
654824   3/1986  Switzerland.

*Primary Examiner*—Marianne M. Cintins
*Assistant Examiner*—Rebecca Cook
*Attorney, Agent, or Firm*—William T. Han

[57] ABSTRACT

The present invention provides BU-4641V of the formula:

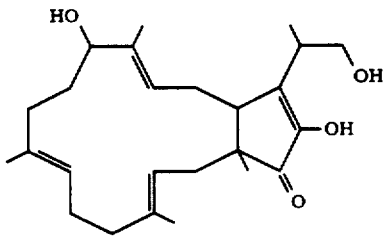

This invention also provides a biologically pure culture of BU-4641V producing Arthrinium sp. FA1744. Another aspect of the invention provides a process for preparing BU-4641V. Yet further aspect of the present invention provides a method for treating mammalian tumors and bacterial or viral infections.

2 Claims, 4 Drawing Sheets

BU-4641V, AN ANTIBACTERIAL, ANTIVIRAL AND ANTITUMOR ANTIBIOTIC

CROSS REFERENCE

This application is a continuation-in-part of U.S. Patent application Ser. No. 07/843,659, filed on Feb. 28, 1992, now abandoned, which is herein incorporated by reference in its entirety.

BACKGROUND OF INVENTION

The field of present invention is novel antibiotic BU-4641V having antibacterial, anti-tumor (anti-cancer) and antiviral activities.

Acquired immunodeficiency syndrome (AIDS) is an infectious disease characterized by severe impairment of the cell-mediated immune system in the patient. Recent epidemiological and molecular biochemical research results evidently indicate that human immunodeficiency virus (HIV) is the major etiological agent of AIDS. Many anti-HIV agents have been reported such as antibodies to the virus or cellular receptors, sulphated polysaccharides having an ability to block adsorption of virions to target cells, 3'-azido-2',3'-dideoxythymidine (AZT), 2',3'-dideoxycytidine (DDC) and tetrahydro-imidazo-[4,5,1-jk][1,4]-benzodiazepin-2(1H)-one and -thione (TIBO) for inhibiting a reverse transcriptase-associated process (R. Pauwels, et al., *Potent and selective inhibition of HIV-I replication in vitro by a novel series of TIBO derivatives*, Nature, 343, pp 470–474, 1990), synthetic peptides for inhibiting viral protease (C. Debouck & B. W. Metcalf, *Human immunodeficiency virus protease: a target for AIDS therapy*, Drug Development Research, 21, pp 1–17, 1990), and castanospermine for inhibiting myristoylation and glycosylation of virions (See review of: H. Mitsuya, R. Yarchoan & S. Broder, Molecular targets for AIDS therapy, Science, 249, pp 1533–1544, 1990).

The HIV envelope glycoprotein, gp-160, is essential for the viral entry into cells. The gp-120 expressed on HIV-infected cells interact with the CD4 surface antigen on target cells. This interaction precedes a post-binding fusion event mediated by the HIV transmembrane gp-41, leading to a multinucleated giant cell called syncytium. As described above, the sulphated poly-saccharides such as dextran sulphate clearly inhibit this syncytium formation, and consequently the in vitro HIV infection. From this point of view, syncytium formation inhibitors are potential anti-HIV agents. We have now isolated, from fermentation broths of Arthrinium sp. FA1744, BU-4641V with heretofore unknown structure and with stronger syncytium inhibitory property than that of dextran sulfate.

Further, BU-4641V has been found to promote tubulin polymerization, a property which confers taxol, a well-known anticancer drug, its anti-tumor ability. Thus, BU-4641V has anti-tumor properties. Additionally, BU-4641V was also found to have anti-bacterial properties.

SUMMARY OF INVENTION

The present invention provides BU-4641V of the formula:

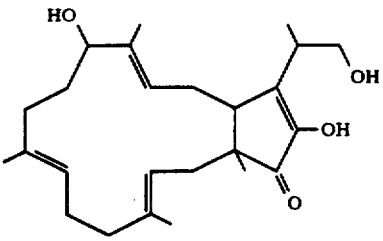

A further aspect of the invention provides a biologically pure culture of BU-4641V producing Arthrinium sp. FA1744.

Yet another aspect of the invention provides a process for preparing BU-4641V which comprises cultivating the antibiotic-producing strain of Arthrinium sp. FA1744 or a mutant or a variant thereof under submerged and aerobic conditions in a medium containing assimilable sources of carbon and nitrogen.

Yet further aspect of the present invention provides a method for treating bacterial or viral infections which comprises administering to a mammal so afflicted with an antibacterial or antiviral effective amount of BU-4641V.

Yet another aspect of the invention provides a method for treating mammalian tumor which comprises administering to a mammal so afflicted with an anti-tumor effective amount of BU-4641V.

Yet another aspect of the invention provides a pharmaceutical formulation comprising BU-4641V and one or more pharmaceutically acceptable carriers, exicipients or diluents therefor.

DETAILED DESCRIPTION OF INVENTION

Figure 1:
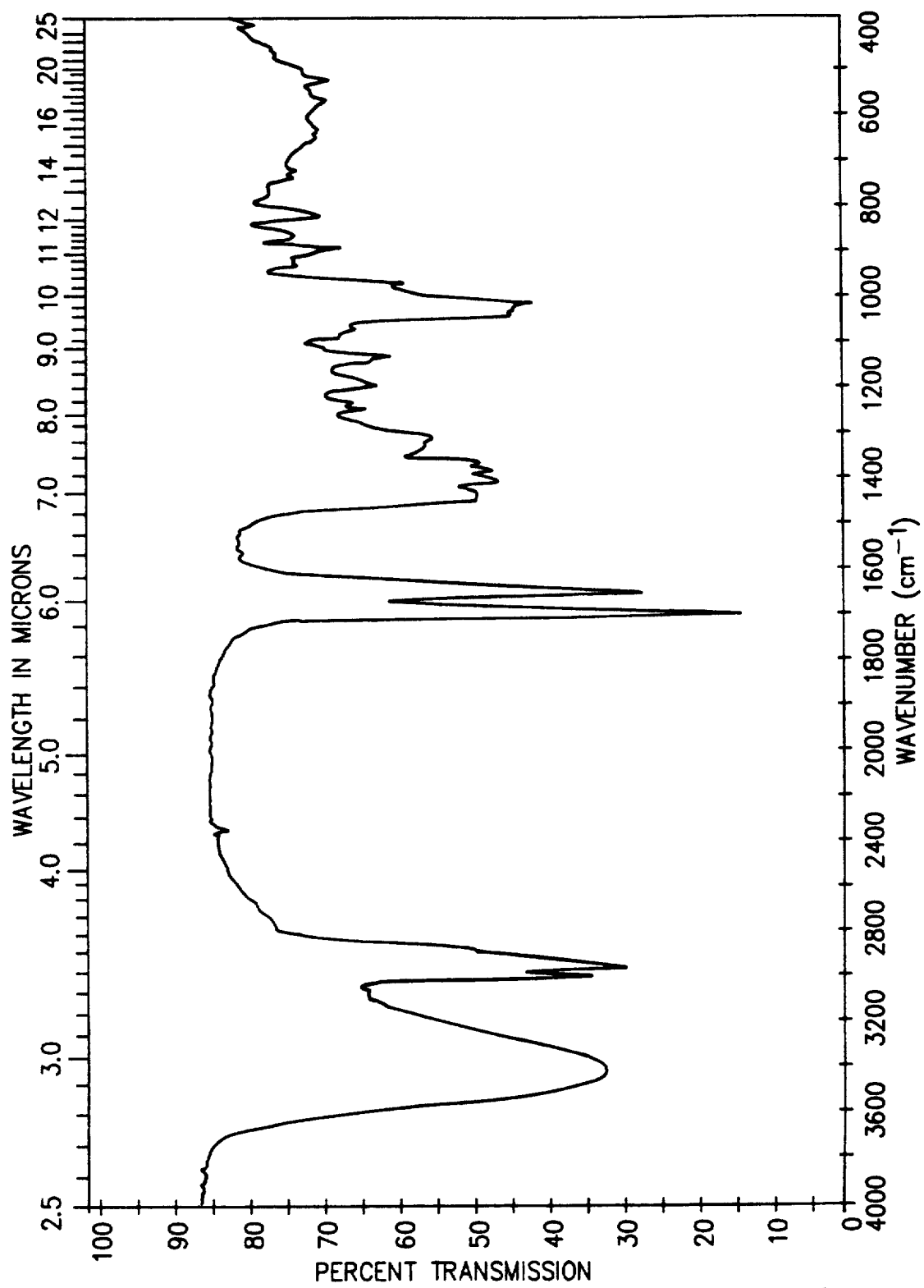
FIG. 1 is the IR spectrum of BU-4641V.

The present invention provides BU-4641V of the formula:

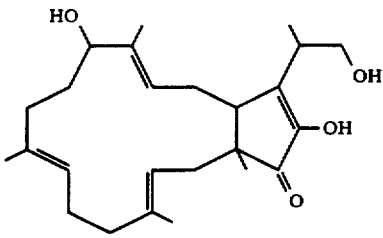

Also included within the scope of the present invention are pharmaceutical formulations (compositions) for BU-4641V. Preferably these formulations are in unit dosage forms such as tablets, pills, capsules, powders, granules, sterile parenteral solutions or suspensions, or suppositories for oral, parenteral or rectal administration. For preparing solid formulations such as tablets, the principal active ingredient is mixed with a pharmaceutical carrier, i.e. conventional tableting ingredients such as corn starch, lactose, sucrose, sorbitol, talc, stearic acid, magnesium stearate, dicalcium phosphate, gums, and other pharmaceutical diluents, e.g. water, to form a solid preformulation composition containing a homogeneous mixture of BU-4641V. When referring to these preformulation compositions as homogeneous, it is meant that the active ingredient is dispersed evenly throughout the formulation so that the formulation may be readily subdivided into equally effective unit dosage forms such as tablets, pills, capsules, and the like. This solid preformulation composition is then subdivided into unit dosage forms of the type described above containing from 0.1 to about 500 mg of the active ingredient of the present invention. The tablets or pills of the novel formulation can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like.

The liquid forms in which the novel formulation of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

A further aspect of the invention provides a biologically pure culture of BU-4641V producing Arthrinium sp. FA1744.

Yet another aspect of the invention provides a process for preparing BU-4641V which comprises cultivating the antibiotic-producing strain of Arthrinium sp. FA1744 or a mutant or a variant thereof under submerged and aerobic conditions in a medium containing assimilable sources of carbon and nitrogen.

BU-4641V PRODUCING ORGANISM

Taxonomy

Strain FA1744 was isolated from a soil sample collected in Akiyoshidoh, Yamaguchi prefecture, Japan on Feb. 11, 1990.

The determination of color name and of color code was made by comparison the culture with color chips (numbers in parentheses) from the Manual of Color Names (Japan Color Enterprise Co., Ltd., 1987).

Morphology

Strain FA1744 showed good growth on potato dextrose agar, potato starch agar, corn meal agar and malt extract agar. Conidial structures are more abundantly produced on ½ malt extract agar rather than on the four agar media described above. On ½ malt extract agar, the mycelium is partly superficial, partly immersed; the superficial part is composed of a network of branched structures. The mycelium is beige gray (401), septate, smooth and 2-8 μm in width. Conidiophores are arising from conidiophore mother cells which are subspherical or ampulliform-shaped, being 5-8×3-5 μm in size. They are hyaline and refractive, measuring more than 30 μm long and 1.5-3 μm in thick with brown transverse septa. Conidia are dark brown, lenticular-shaped with a colorless band at the junction of the two sides and 7-9 μm in diameter. There is no evidence of formation of stroma, setae and hyphopodia.

Cultural Characteristics

The macroscopic properties of strain FA1744 on various agar media were determined after incubation for 14 days at 25° C.

On malt extract agar, colonies grow rather rapidly attaining 80-85 mm in diameter and grayish olive (168) in color. The colony surface is thick and floccose. The colony reverse is light yellowish brown (92) to dark grayish brown (124). No diffusible pigment is produced.

On potato dextrose agar, colonies grow rather rapidly attaining 60-63 mm in diameter and grayish olive (169) to greenish gray (412) with the surface floccose in appearance. The reverse color is dark grayish yellow (155) to dark grayish brown (124). pigment in agar is lacking.

On potato starch agar, colonies grow rather rapidly, attaining 60-65 mm in diameter and grayish olive (170-171). The colony reverse is soft yellow (147) to dark grayish brown (124). No pigment in agar is formed. On corn meal agar, colonies grow rapidly, attaining 80-83 mm in diameter and grayish olive (170). The surface of colonies is thin and cottony. The reverse is colorless.

On Czapek solution agar, this strain forms poor-growing and yellowish brown (97) colonies, reaching 6-mm in diameter. On oat meal agar, colonies grow rather slowly attaining 28-30 mm in diameter and grayish olive (172). The reverse is colorless.

Physiological Characteristics

Strain FA1744 shows good growth at 10-30° C. on malt extract agar. The optimum temperature for growth is 20-25° C.

On the basis of the morphological observation, strain FA1744 is assigned to the hyphomycete genus Arthrinium Kunze, with description of Arthrinium by Ellis (M. B. Ellis, *Dematiceous hyphomycetes*, pp. 567-575, Common Wealth Mycological Institute, Kew, Surrey, England, 1971; M. B. Ellis, *More dematiaceous hyphomycetes*, pp. 477-478, Common Wealth Mycological Institute, Kew, Surrey England, 1976) and identified as a species of Arthrinium.

Strain FA1744 was deposited at the American Type Culture Collection, 12301 Parklawn Drive, Rockville, Md. on Jan. 31, 1992. The culture was accepted for deposit under the Budapest Treaty on the International Recognition of the Deposit of Microorganism for the Purpose of Patent Procedure. Strain FA1744 has the accession number ATCC 74132.

GENERAL FERMENTATION PROCEDURE

The general procedures which have been used for the fermentation of other antibiotics from fungi are applicable to the present invention. For example, BU-4641V may be produced by cultivating the BU-4641V producing strain of Arthrinium sp. FA1744 or a mutant or a variant thereof, under a submerged aerobic condition in an aqueous nutrient medium.

The nutrient medium contains an assimilable carbon source, for example, sucrose, lactose, glucose, rhamnose, fructose, mannose, melibiose, glycerol or soluble starch to name a few.

The nutrient medium should also contain an assimilable nitrogen source such as fish meal, peptone, soybean flour, peanut meal, cottonseed meal, corn steep liquor, yeast extract or ammonium salts. Other inorganic salts such as sodium chloride, potassium chloride, calcium carbonate, phosphates, etc. are added if necessary. Trace elements such as copper, manganese, etc. are added to the medium if required, or they may be supplied as impurities of other constituents of the medium.

Production of BU-4641V can be effected at any temperature conducive to satisfactory growth of the producing organism, e.g. 15°-45° C., but it is preferable to conduct the fermentation at 21°-45° C., and most preferably at 25°-32° C. A neutral pH is preferably employed in the medium and the production of the antibiotic is carried out generally for a period of about five to fourteen days.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation medium for large scale production of the antibiotic. The medium in which the vegetative inoculum is produced can be the same as, or different from that utilized in the tank as long as it is such that a good growth of the producing organism is obtained. Agitation during the fermentation can be provided by a mechanical impeller, and conventional antifoam agents such as lard oil or silicon oil can be added if needed.

DESCRIPTION OF SPECIFIC EMBODIMENTS

The following specific embodiments are intended to be merely illustrative and are not intended to limit the scope of the invention. For example, it is not the intention of this invention to limit the use to the particular Arthrinium sp. FA1744 or to organisms fully answering the above description for the production of BU-4641V. Rather, this invention includes other BU-4641V producing strains or mutants or variants of said organism which can be produced from the described organism by known means such as X-ray radiation, ultraviolet radiation, treatment with nitrogen mustard, phage exposure, and the like.

Except otherwise noted, v/v refers to volume/volume.

Fermentation of BU-4641V

A well grown agar slant of Arthrinium sp. FA1744 was inoculated into a 500-ml Erlenmeyer flask containing 100ml of a seed medium consisting of soluble starch (Nichiden Kagaku) 2.0%, glucose 0.5%, NZ-case (Humko Scheffield) 0.3%, yeast extract (Oriental yeast) 0.2%, fish meal D30X (Banyu Eiyo) 0.5% and CaCO3 0.3% (pH 7.0, before sterilization).

The seed flask was incubated for 4 days at 28° C. on a rotary shaker (200 rpm) and 5 ml of this culture was transferred into a 500-ml Erlenmeyer flask containing 100 ml of a production medium which consisted of mashed potato (Yuki-jirushi Nyugyo) 0.1%, glucose 0.3%, corn meal (Sakura Meal Co.) 2.0%, cane molasses (Nihon Tensaitoh) 1.0%, fish meal (Hokuyo Siusan) 0.5%, wheat bran 1.0%, NaCl 0.3% and CaCO3 0.3% (pH 7.0, before sterilization). The fermentation was carried out at 28° C. for 6 days on the rotary shaker (200 rpm). The BU-4641V production in the fermentation broth was determined by the syncytium formation inhibitor assay method. After 6-day fermentation, the production of BU-4641V reached the maximum potency (35 μg/ml).

Isolation

The cultured broth (9 L) was filtered with the aid of diatomaceous earth. The mycelial cake was extracted with methanol (2×1 L), and the combined extracts were concentrated in vacuo to about 200 mL. The concentrate was extracted with ethyl acetate (200 mL), and the extract evaporated to give 3.6 g of brown oil. It was chromatographed on a silica gel column (Merck Kieselgel 60, 500 mL) with methylene chloride (1 L) and then with methylene chloride-methanol (95:5, 2 L). The eluate was collected in 20 g-fractions; each fraction was monitored by HPLC (YMC A-301-3 Yamamura Chem. Lab. Co.; eluant, 50% aqueous acetonitrile; flow rate 1.2 mL/minute; detection UV at 254 nm: retention time 4.5 minutes) and also by the syncytia inhibition assay. Evaporation of the collected active fractions (Nos. 46–63) yielded a yellow amorphous powder (1.84 g). The powder was dissolved in aqueous acetonitrile (20 mL) and charged on a column of reversed phase silica gel (150 mL, YMC-GEL ODS-A 60-350/250 Yamamura Chem. Lab. Co.). The column was developed with 30% aqueous acetonitrile (1 L) and then with 50% aqueous acetonitrile (1.5 L). The desired compound was eluted with 50% aqueous acetonitrile and the appropriate eluates were combined and evaporated to give 316 mg of light-yellow powder. The semi-pure sample (310 mg) was purified by Sephadex LH-20 (800 mL) column chromatography with methylene chloride-methanol (1:1). The appropriate fractions were combined and evaporated to give a colorless amorphous powder (263 mg) of pure BU-4641V.

Physico-chemical properties of BU-4641V

Figure 2:
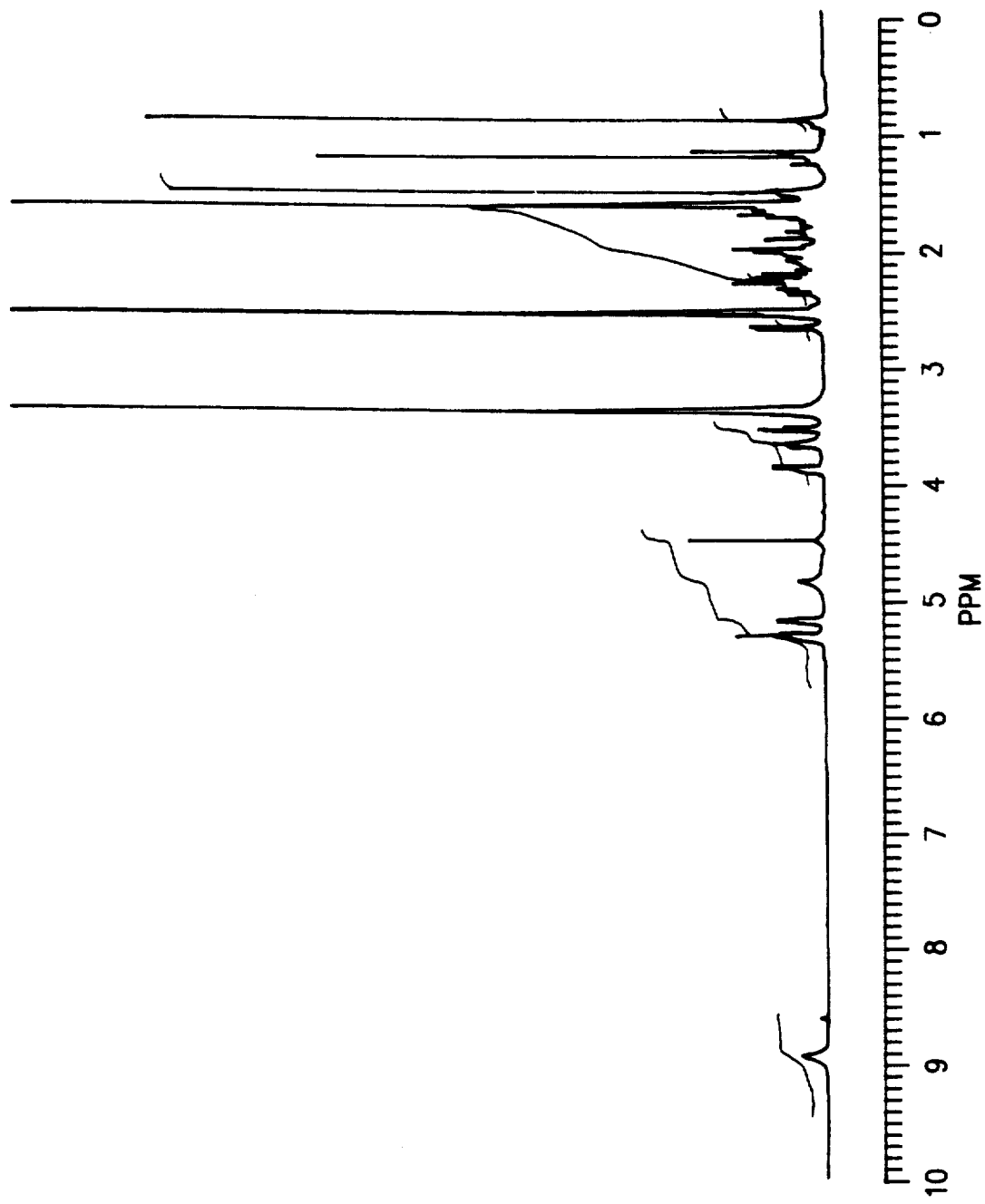
FIG. 2 is the $^1$H-NMR spectrum of BU-4641V.
Figure 3:
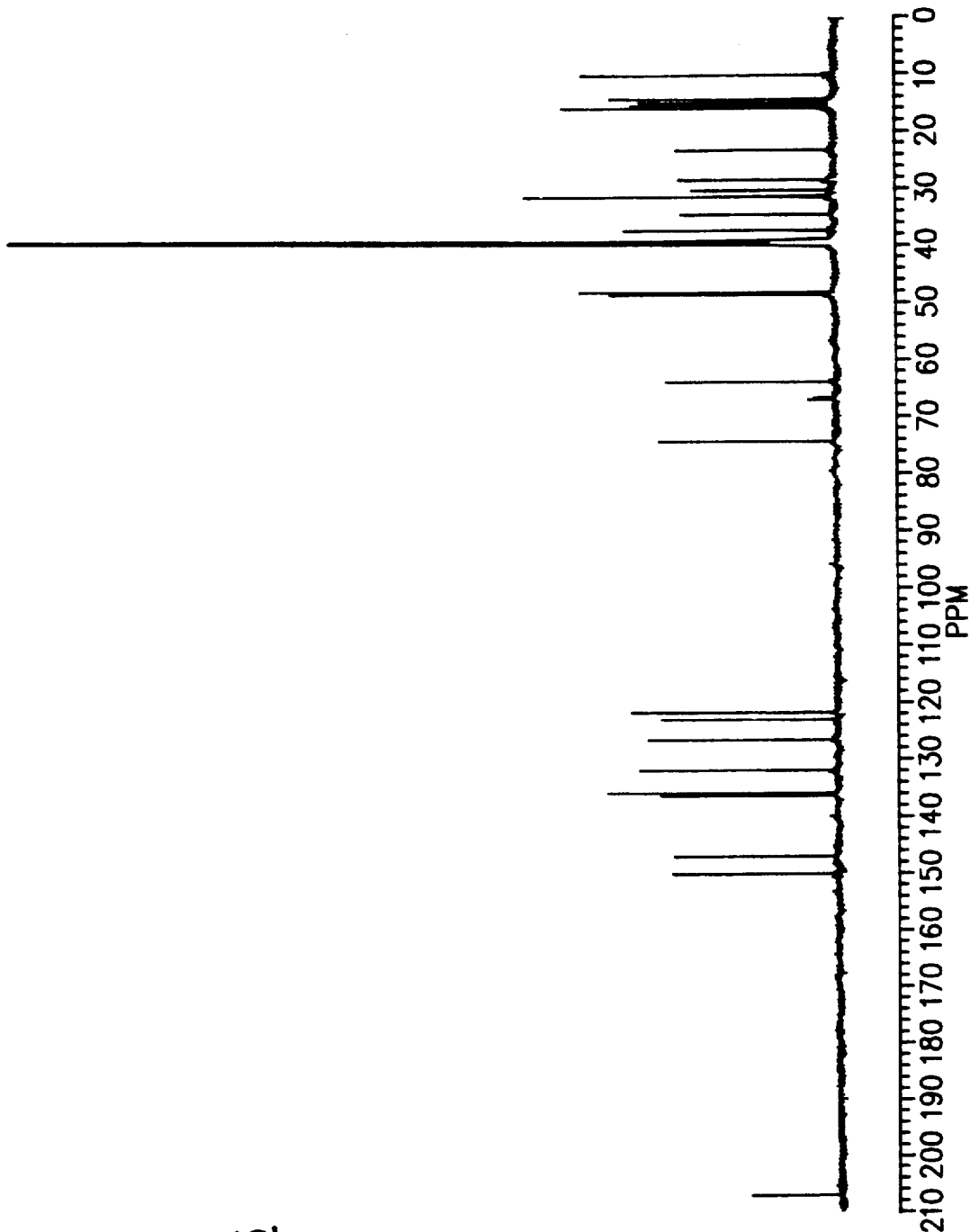
FIG. 3 is the $^{13}$C-NMR spectrum of BU-4641V.

BU-4641V was isolated as a white amorphous powder. It was soluble in dimethyl sulfoxide, methanol, methylene chloride, ethyl acetate and alkaline water (such as 0.1 N NaOH), but insoluble in hexane and water. It gave positive responses to iodine vapor, sulfuric acid and ferric chloride tests, but negative responses to Rydon-Smith, Dragendorff and anthrone-sulfuric acid tests on silica gel TLC plate. Other physico-chemical properties of BU-4641V are summarized in Table 1. Together with the IR, $^1$H-NMR, and $^{13}$C-NMR spectrometric data in FIGS. 1 to 3, respectively, these physico-chemical properties set BU-4641V apart from any known antibiotics.

TABLE 1.

| Physico-chemical properties of BU-4641V | |
|---|---|
| Nature | Colorless amorphous powder |
| M.P. | 72° C. (gradual decomposition) |
| $[\alpha]_D^{22}$(C 0.5, CHCl$_3$) | +26° |
| Molecular formula | C$_{25}$H$_{38}$O$_4$ |
| High Resolution-Mass Spectrum (m/z) | |
| Calcd for C$_{25}$H$_{38}$O$_4$ | 402.2752 |
| Found | 402.2761 |
| Microanalysis | C$_{25}$H$_{38}$O$_4$.H$_2$O |
| Calcd for | C, 71.39; H, 9.59 |
| Found | C, 71.77; H, 9.30 |

TABLE 1.-continued

Physico-chemical properties of BU-4641V

| | |
|---|---|
| UV $\lambda_{max}$ nm ($\epsilon$) | 264 (10800) in MeOH |
| | 298 (8500) in alkaline |
| | MeOH (0.01N NaOH) |
| IR $\nu$ (KBr, cm$^{-1}$) | 3400, 1700, 1655, 1450, |
| | 1405, 1040, 1020 |
| HPLC*$^1$ Rt (minutes) | 4.5 |
| TLC*$^2$ Rf | 0.41 |

*$^1$YMC A-301-3 Yamamura Chem. Lab. Co.; eluant, CH$_3$CN/H$_2$O, 1/1; flow rate 1.2 mL/minute; detection UV at 254 nm
*$^2$Merck Kieselgel 60; CH$_2$Cl$_2$/CH$_3$OH, 10/1; detection by I$_2$

Syncytium formation inhibition assay

The assay system for screening anti-syncytium formation agents consists of two cell lines, recombinant vaccinia virus-infected BSC-1 cells (gp-120 expressed) and HeLa-T4 cells (CD4 antigen expressed). Two cell lines were mixed together in the presence or absence of an inhibitor and the number of syncytia formed with 3–5 hours was scored.

Cultivation of Assay Cells

CD4-bearing HeLa (HeLa-T4) cells (P. J. Maddon, et al., *The T4 gene encodes the AIDS virus receptor and is expressed in the immune system and the brain*, Cell, 47, pp 333–348, 1986) were grown in Dulbecco modified Minimum Essential Medium (D-MEM, GIBCO) supplemented with 10% heat-inactivated fetal bovine serum (FBS, GIBCO) and 1 mg/ml geneticin (GIBCO). BSC-1 cells were grown in Eagle(E)-MEM (Nissui Pharmaceutical, Tokyo) supplemented with 10% FBS and 50 µg/ml amikacin (Bristol-Myers Squibb).

PREPARATION OF HIV gp-120 EXPRESSING BSC-1 CELLS

A monolayer culture of BSC-1 cells (3-day-old confluency) in a T-75 LUX flask (Sanko Junyaku, Tokyo) was inoculated by recombinant vaccinia virus (S. L. Hu, S. G. Kosowski, J. M. Dalrymple, *Expression of AIDS virus envelope gene in recombinant vaccinia viruses*, Nature, 320, pp 537–540, 1986) at an MOI (Multiplicity of infection) of 0.01. After viral adsorption within one hour, the viral inoculum was removed by aspiration and the virus-infected cells were added 8 ml of E-MEM and incubated at 37° C. for further 20 to 24 hours in a humidified 5% CO$_2$ and 95% air environment. After the infected cells were removed from the plastic flask surface using a cell scraper, the syncytium formation titer of the cell suspension, designated HIV gp-120 expressing BSC-1 cells, was determined to be 6×10$^4$ syncytia per milliliter by the 2-serial dilution method using HeLa-T4 cells as the test cells.

Syncytium formation inhibition assay

A HeLa cell suspension (100 µl containing 3×10$^4$ cells) was seeded in each well of the 96-well microtiter-plate and grown at 37° C. for 20 to 24 hours in a humidified 5% CO$_2$ and 95% air environment. The old medium was removed and replaced by 50 µl of the fresh E-MEM supplemented with 10% FBS which contained a test sample at various concentrations. Then the HIV gp-120 expressing BSC-1 cell suspension was diluted at 1:15. Fifty microliters of the dilution was added to each well of the 96-well microtiterplate. After incubation at 37° C. for 3–5 hours, the medium in each well was removed by aspiration. Cells were stained with 50 µl Giemsa solution (Wako Pure Chemicals, Osaka) and were washed 3 times with tap water. Number of syncytia in each well was scored under a microscope at a magnification of 40. Syncytium inhibitory activity of the compound is expressed in ID$_{50}$ (50% inhibitory dose) which is defined as the minimal concentration of the compound required to reduce syncytia formation by 50% as compared to the inhibitor-untreated control.

Dextrane sulfate was used as a reference compound for syncytium formation inhibitory activity. The result in Table 1 shows that BU-4641V has more potent syncytium inhibitory activity (ID$_{50}$: 0.46 µg/ml) than dextran sulfate.

TABLE 1

Comparative syncytium inhibitory activities of BU-4641V and dextran sulfate

| Compound | Syncytium inhibitory activity ID$_{50}$ (µg/ml) |
|---|---|
| BU-4641V | 0.46 |
| Dextran sulfate | 12.0 |

INHIBITION OF HUMAN T CELL LYMPHOTROPIC VIRUS TYPE III BY BU-4641V

Human T cell lymphotropic virus type III (HTLV-III)/lymphadenopathy-associated virus is the etiologic agent of the acquired immune deficiency syndrome (AIDS) and AIDS-related complex. The effect of BU-4641V on the HTLV-III/lymphadenopathy-associated virus infection was quantitatively studied by HTLV type I-carrying MT-4 cells. (Nakashima, H. et al., *Antimicrobial Agents & Chemotherapy*, 30, pp 933–937, 1986).

Assay

An HTLV type I-Carrying cell line, MT-4, was maintained in RPMI 1640 medium supplemented with 10% fetal calf serum, 100 IU of penicillin G per ml and 100 µg of streptomycin per ml at 37° C. in a CO$_2$ incubator. HTLV-III$_B$ was obtained from the supernatant of the Molt-4/HTLV-III$_B$ culture. The titer of this virus preparation was 3.0×10$^5$ PFU/ml. MT-4 cells were infected with 0.01 MOI of HTLV-III$_B$. The infected cells resuspended in fresh medium were mixed with a test sample solution (or medium itself for control) to give 2.5×10$^4$ cells in a 200 µl volume and incubated at 37° C. for 5 days. The surviving cells were measured by the MTT (3-(4,5-dimethylthiazol-2-yl)-2,5-diphenyltetrazolium bromide) method (R. Pauwels et al., *J. Virol Methods*, 20, pp 309–321, 1988).

$$\text{Inhibition rate} = \frac{(ODt)_{HIV} - (ODc)_{HIV}}{(ODc)_{mock} - (ODc)_{HIV}}$$

($ODt)_{HIV}$: with the test sample solution
($ODc)_{HIV}$: without the test sample solution
($ODc)_{mock}$: uninfected MT-4 without the test sample solution Fifty percent effective concentration (EC$_{50}$) was obtained from the inhibition rates. Cytotoxicity of the sample was obtained in a separate experiment using virus-uninfected MT-4 cells and the 50% cytotoxicic concentration (CC$_{50}$) was calculated.

As shown in Table 2, BU-4641V was found to be more active than dextran sulfate against HTLV-III and has a potential use for anti-AIDS therapy.

TABLE 2

| Compound | CC$_{50}$ μg/ml | EC$_{50}$ μg/ml |
|---|---|---|
| BU-4641V | 37.8 | 0.78 |
| Dextran sulfate | >1000 | 1.4 |

Further study has shown that BU-4641V only partially blocks the acute infection of HIV-1 IIIb in the CEM-SS cells with an IC$_{50}$ of 10 μM and CC$_{50}$ of 84 μM. The compound does not affect the binding of HIV envelope protein gp120 to T cells. The anti-HIV activity of this agent seems to be host-dependent suggesting that the functional target of BU-4641V may be a host factor.

Promotion of Tubulin Polymerization

Due to the association of tubulin polymerization/depolymerization with cell fusion, BU-4641V was tested for its effect on tubulin polymerization using thrice-cycled microtubule protein (3XMTP) and spectrophotometric measurement. Briefly, tubulin was purified from calf brain extracts by three cycles of polymerization at 35° C. in the presence of 1 mM GTP+2.5 mM ATP, and depolymerization at 4° C. in PM buffer pH 6.6 (0.1 M PIPES, 2 μM EGTA, 1 μM MgSO$_4$ and 2 μM DTT) containing various concentrations of glycerol as described previously (Williams R. C. and J. C. Lee 1982 *Methods in Enzymology* 85: pp. 376–385). The tubulin polymerization assay was carried out using 3XMTP in PM buffer containing 0.4 M of glycerol in the presence of test-compound. The polymerization was quantitated by Shimadzu spectrophotometer (Model No. UV 2100U) at 350 nm. Effect of compound on the kinetics of tubulin polymerization was followed for 20 minutes using taxol as a positive control and DMSO as a negative control. Compound in PM buffer +0.4 M glycerol (no MTP) served as buffer (negative) controls.

Figure 4:
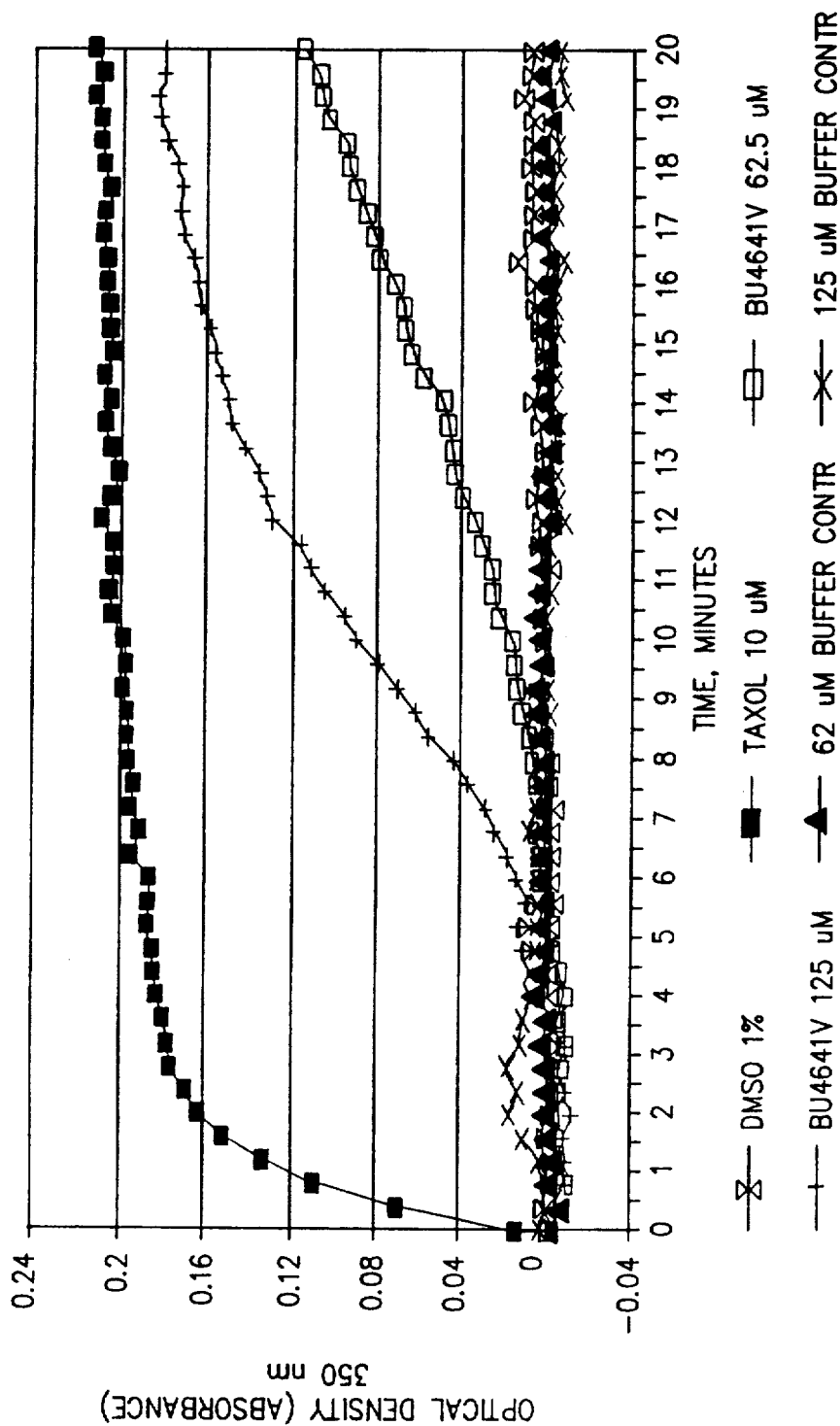
FIG. 4 is a graph showing tublin polymerization activity of BU-4641V together with taxol as a reference.

Our results (Table 3 and FIG. 4) show that BU-4641V promotes tubulin polymerization in a dose dependent manner. Compared to taxol, BU-4641V catalyzes tubulin polymerization at a slower initial rate, but the peak level of polymerization stimulated by 100 μM of BU-4641V is similar to that of 10 μM taxol. In contrast to taxol, the promotion of tubulin polymerization by BU-4641V can be reversed by treatment with CaCl$_2$. GTP is also known to reversibly promote tubulin polymerization. However, GTP is only active on tubulin in the presence of microtubule associated proteins (MAPS), and they are not present in sufficient quantity in 3XMTP. Thus, the biological activity of BU-4641V is distinct from GTP. The tubulin polymerization promoting effect has been confirmed by electron microscopic observation of microtubule assembly in 3XMTP containing 100 μM of BU-4641V. Finally, immunofluorescence studies show that BU-4641V, like taxol, also induces tubulin bundling around nuclei in human colon cells.

In summary, it has been demonstrated that BU-4641V reversibly stimulates polymerization of purified tubulin protein using techniques of spectrophotometry, electron microscopy and immunofluorescence staining. Thus, BU-4641V, which shares a similar tubulin polymerization stimulatory activity as taxol, is useful as an anti-cancer agent.

TABLE 3

| | Conc., uM or (%) | Relative Slope, % | Relative Peak, % |
|---|---|---|---|
| DMSO | 1(%) | 1 | 5 |
| Taxol | 10 | 100 | 100 |
| BU4641V | 25 | 5 | 19 |
| BU4641V | 125 | 21 | 78 |
| DMSO | 1(%) | 1 | 3 |
| Taxol | 10 | 100 | 100 |
| BU4641V | 62.5 | 9 | 55 |
| BU4641V/Buffer Control | 62.5 | 0 | 1 |
| BU4641V | 125 | 20 | 85 |
| BU4641V/Buffer Control | 125 | −1 | −2 |
| DMSO | 2(%) | 3 | 24 |
| Taxol | 10 | 100 | 100 |
| BU4641V | 50 | 12 | 64 |
| BU4641V | 100 | 20 | 93 |
| BU4641V | 200 | 25 | 87 |

Relative Slope = 100 × (Initial Slope of Sample)/(Initial Slope of Taxol)
Relative Peak = 100 × (20-min Peak Activity of Sample)/(20-min Peak Activity of Taxol)

Antibacterial Activity

Table 4 lists the antibacterial MIC values for BU-4641V.

In conclusion, the tests described herein demonstrate the BU-4641V is useful in treating viral and bacterial infections. Thus further aspect of the present invention provides a method for treating bacterial or viral infections which comprises administering to a mammal so afflicated an antibacterial or antiviral effective amount of BU-4641V.

TABLE 4

| Organism | MIC (μg/ml) |
|---|---|
| S. aureus FDA 209P | 25 |
| S. aureus Smith | 100 |
| S. aureus IPM-24 (MRSA) | 100 |
| S. epidermidis 11-1168 | 50 |
| S. epidermidis 11-1230 | 100 |
| E. faecalis A9808 | 100 |
| E. faecium A24817 | 100 |
| M. luteus PCI 1001 | 100 |
| B. subtilis PCI 219 | 100 |
| E. coli Juhl A15119 | >100 |
| E. coli 255 | >100 |
| K. pneumoniae PCI 602 | >100 |
| P. mirabilis IFO 3849 | >100 |
| P. vulgaris IPM-13 | >100 |
| M. morganii 1510 | >100 |
| M. morganii 1510/9 | >100 |
| P. rettgeri IPM-14 | >100 |
| E. cloacae IPM-12 | >100 |
| S. marcescens IPM-15 | >100 |
| S. marcescens IPM-16 | >100 |
| C. freundii GN7391 | >100 |
| P. aeruginosa A9843A | >100 |
| P. aeruginosa A20599 | >100 |
| P. aeruginosa KKA19 | >100 |
| P. aeruginosa IPM-8 | >100 |
| P. aeruginosa IpM-9 | >100 |
| X. maltophilia GN12873 | >100 |
| X. maltophilia No. 661 | >100 |
| P. cepacia No. 651 | >100 |
| P. cepacia A21213 | >100 |
| C. terrigena IFO 12685 | 12.5 |

Method: agar dilution technique,
Medium: Nutrient agar, pH 7.0, Incubation temp: 32° C.,
Incubation time: 18 hrs, Inoculum size: 10$^5$ cells/ml

What is claimed is:

1. BU-4641V of the formula

11

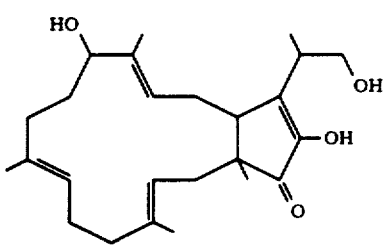

2. A pharmaceutical formulation which comprises as an ingredient BU-4641V as claimed in claim 1, which further contains one or more pharmaceutically acceptable carriers, excipients or diluents therefor.

* * * * *

12

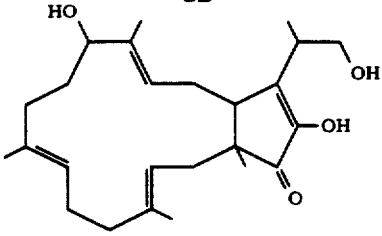

2. A pharmaceutical formulation which comprises as an ingredient BU-4641V as claimed in claim 1, which further contains one or more pharmaceutically acceptable carriers, excipients or diluents therefor.

* * * * *

UNITED STATES PATENT AND TRADEMARK OFFICE
CERTIFICATE OF CORRECTION

PATENT NO. : 5,266,600

DATED : November 30, 1993

INVENTOR(S) : Osamu Tenmyo, et al

It is certified that error appears in the above-indentified patent and that said Letters Patent is hereby corrected as shown below:

On the title page:

Item [75]   Please delete as inventors:
"Pin-Fang Lin, Branford: and Stephen W. Mamber, Wethersfield, both of Conn."

Signed and Sealed this

Fourteenth Day of March, 1995

Attest:

BRUCE LEHMAN

Attesting Officer

Commissioner of Patents and Trademarks